United States Patent
Cole et al.

(10) Patent No.: US 9,815,856 B2
(45) Date of Patent: Nov. 14, 2017

(54) FUNCTIONALIZED PRIMARY ALKYLTRIFLUOROBORATE SALTS AND METHOD FOR MAKING THE SAME

(71) Applicant: SAN DIEGO STATE UNIVERSITY FOUNDATION, San Diego, CA (US)

(72) Inventors: Thomas E. Cole, San Diego, CA (US); Gloria Hincapie, Santa Ana, CA (US); Stewart C. Polk, San Diego, CA (US); David Zillman, San Clemente, CA (US)

(73) Assignee: San Diego State University Research Foundation, San Diego, CA (US)

( * ) Notice: Subject to any disclaimer, the term of this patent is extended or adjusted under 35 U.S.C. 154(b) by 0 days.

(21) Appl. No.: 15/122,795

(22) PCT Filed: Mar. 5, 2015

(86) PCT No.: PCT/US2015/019063
§ 371 (c)(1),
(2) Date: Aug. 31, 2016

(87) PCT Pub. No.: WO2015/134811
PCT Pub. Date: Sep. 11, 2015

(65) Prior Publication Data
US 2017/0066786 A1    Mar. 9, 2017

Related U.S. Application Data

(60) Provisional application No. 61/949,056, filed on Mar. 6, 2014.

(51) Int. Cl.
*C07F 5/02* (2006.01)

(52) U.S. Cl.
CPC ................................. *C07F 5/025* (2013.01)

(58) Field of Classification Search
CPC ...................................................... C07F 5/025
USPC ............................................................ 568/6
See application file for complete search history.

(56) References Cited

PUBLICATIONS

CID 72508936 by PubChem.*

* cited by examiner

*Primary Examiner* — Deborah D Carr
(74) *Attorney, Agent, or Firm* — Knobbe, Martens, Olson & Bear LLP

(57) ABSTRACT

The invention provides methods for preparing boronic acids, for example, primary alkyl or alkenyl boronic acids, and alkali metal alkyl trifluoro borate salts, as described herein, wherein the primary alkyl boronic acids and the potassium alkyl trifluoroborate salts can contain one or more unprotected functional groups.

18 Claims, No Drawings

FUNCTIONALIZED PRIMARY ALKYLTRIFLUOROBORATE SALTS AND METHOD FOR MAKING THE SAME

INCORPORATION BY REFERENCE TO ANY PRIORITY APPLICATIONS

This application is the National Phase Entry of PCT International Application No. PCT/US2015/019063, filed Mar. 5, 2015 which claims priority to U.S. Provisional Patent Application No. 61/949,056, filed Mar. 6, 2014, each of which are incorporated herein by reference in their entirety.

BACKGROUND

Boronic acids, trifluoroborate salts and the corresponding N-methylimidoacetate (MIDA) complexes are used as synthetic intermediates for the synthesis of complex molecules using the Suzuki-Miyaura palladium catalyzed cross-coupling reaction. This reaction is used extensively in biomedical and pharmaceutical research. While a large number of aryl, heteroaryl and vinylboronic compounds are readily available, only a few alkyl and fewer still functionalized alkylboronic derivatives are available, There are few methods that can be used to directly prepare boronic derivatives via hydroboration. These methods either used the strongly Lewis acidic haloboranes. $HBX_2$ or the very sluggish catecholborane or pinacolborane. In both cases, these reagents reduce many functional groups. In general, dialkylborane are somewhat less reaction towards reduction and more selective in hydroborations readily forming the mixed borane, $R_2BR'$. However, are very few methods that allow a selective removal of the two alkyl groups. The best known example of this reaction is the elimination of the isopinocampheyl groups using an aldehyde such as benzaldehyde or acetaldehyde to yield alpha-pinene and the boronic ester. The limitation to using the diisopinocampheylborane, $Ipc_2BH$ is significant reduction of functional groups, cost of the alpha-pinene used to prepare $Ipc_2BH$. Also, the elimination does not always result in the formation of the desired product.

The one group reductive alkylation reaction has been known since the early 1960's. One equivalent of trialkylborane, $R_3B$, is reacted with one equivalent of p-benozoquinone in an aqueous THF solution resulting in the preferential transfer of the more substituted alkyl group for the alkylhydroquinonone (reduction) and formation of a borinic acid, $R_2BOH$. Despite a number of papers no one reported more than a one group transfer.

What is needed is a general method to prepare functionalized primary alkyl trifluoroborates and the corresponding boronic acids or esters without protecting and &protecting the functional group. Such methods would expand the scope and types of compounds that can be prepared using Suzuki-Miyaura reaction. In addition, boronic acids have been demonstrated biological activities and are also used as intermediates in other important organic reactions; therefore the development of methods that avoid laborious protection and deprotection of functional groups in the preparation of boronic acids or esters would significantly aid the field of organic synthesis.

SUMMARY OF THE EMBODIMENTS

Some embodiments of the present application provide methods fur the preparation of primary alkyl boronic acids and potassium alkyl trifluoroborate salts optionally containing protected and unprotected functional groups, using a two group reductive alkylation reaction. Some embodiments are directed to various compounds prepared by these methods, In some embodiments, terminal alkenes containing unprotected functional groups (including, but not limited to, aldehydes, ketones, esters, amides and nitriles) can be cleanly hydroborated with dialkylboranes. In some embodiments, the hydroborating reagents can be based on secondary alkyl groups. In some embodiments, such hydroborating reagents include, as examples, dicyclohexylborane, 9-borobicyclononane, disiamylborane and diisopinocampheylborane. In some embodiments, the functional groups show minimal reduction and the hydroboration reactions form the primary alkyl group in excellent regioselectivity. In some embodiments, the formed mixed borane, $R_2BR'$, can undergo a rapid two-group reductive alkylation with p-benzoquinone, transferring the secondary auxiliary groups in preference to the primary alkyl ones. In some embodiments, addition of potassium hydrogen difluoride converts the alkylhydroquinone ester into the corresponding potassium alkyltrifluoride salt and alkylhydroquinone. In some embodiments, the primary alkyl trifluoroborate salt can be isolated in excellent yields. In some embodiments, the functional groups do not show any indication of reduction and can be used without protecting groups. The salts can be converted into the corresponding alkylboronic acid or ester.

Some embodiments provide methods for hydroborating a terminal alkene or a 2-alkyl alkene comprising contacting a terminal alkene or a 2-alkyl alkene, and a dialkylborane; wherein the terminal alkene or the 2-alkyl alkene comprises an unprotected functional group, to provide a mixed trialkyl borane. In some embodiments, the mixed trialkylborane can have the formula $R_2BR'$, wherein each R is independently alkyl or cycloalkyl, each substituted or unsubstituted by aryl, or two R groups taken together form a cyclic alkyl group, bonded to the boron atom B, wherein the cyclic alkyl is substituted or unsubstituted by aryl; and R' is alkyl or alkenyl having an unprotected functional group.

In some embodiments, the unprotected functional group can be, for example, an aldehyde, ketone, alkyl or aryl carboxylic ester, alkyl or aryl tertiary amide, or a nitrile. The dialkylborane can be, for example, dicyclohexylborane, 9-borobicyclononane (9-BBN), disiamylborane, or diisopinocampheylborane.

In some embodiments, little or no reduction of the functional group occurs (e.g., less than about 10%, less than about 5%, less than about 2%, or less than about 1%, with respect to the initial terminal alkene or a 2-alkyl alkene compound) in the hydroboration. The hydroboration product was prepared with excellent regioselectivity.

Some embodiments include converting the substituted or unsubstituted primary alkyl potassium alkyltrifluoride salt to the corresponding alkylboronic acid or ester.

Some embodiments include employing the alkylboronic acid or ester in a Suzuki-Miyaura coupling reaction.

Some embodiments provide methods for preparing a substituted or unsubstituted primary alkyl boronic acid and an alkali metal alkyl trifluoroborate salt as described herein, wherein the primary alkyl boronic acid and the potassium alkyl trifluoroborate salt contains one or more unprotected functional groups. Some embodiments provide methods for preparing functionalized vinyl trifluoroborate complexes.

Some embodiments provide methods for the Suzuki-Miyaura coupling reaction. Some embodiments provide methods for aromatic and heteroaromatic $sp^2$-$sp^2$ couplings. Some embodiments provide methods for vinyl to vinyl couplings. Some embodiments provide methods for sp²-sp coupling with alkyne groups, alkyl sp³ to sp³, sp³-sp² and sp³-sp couplings.

In one embodiment there is provided a method for synthesizing a substituted or unsubstituted alkylboronic acid or substituted or unsubstituted alkenyl boronic acid, comprising:
a) contacting a dialkylborane with at least one compound selected from the group consisting of a substituted or unsubstituted terminal alkene and a substituted or unsubstituted alkyne to provide a mixed substituted or unsubstituted trialkylborane or a (substituted or unsubstituted alkenyl) dialkylborane;
b) contacting the mixed substituted or unsubstituted trialkylborane or the (substituted or unsubstituted alkenyl) dialkylborane of step a) with at least two equivalents of an α,β-unsaturated ketone to provide a substituted or unsubstituted alkyl boronate diester or a substituted or unsubstituted alkenyl boronate diester;
c) contacting either water or an alcohol with the boronate diester from step b) to quench the reaction and to yield a corresponding boronic acid product or a corresponding alkoxyboronate diester product.

In a further embodiment after step c) the resulting boronic acid or the resulting boronate diester product is further reacted with potassium hydrogen difluoride to yield a substituted or unsubstituted alkyltrifluoroborate salt or a substituted or unsubstituted alkenyltrifluoroborate salt.

In a further embodiment the substituted or unsubstituted terminal alkene or the substituted or unsubstituted alkyne is substituted with a functional group and the functional group is unprotected when it is contacted with the dialkylborane.

In a further embodiment the functional group is selected from the group of non-acidic proton substituents.

In a further embodiment the non-acidic proton substituents are selected from the group consisting of one or more aldehydes, ketones, carboxy esters, nitriles, lactams, lactones, or tertiary amides.

In a further embodiment the substituted or unsubstituted terminal alkene, or the substituted or unsubstituted alkyne, is substituted with a functional group containing one or more acidic protons and these one or more functional groups are also bonded to a protecting group such that the acidic proton on the functional group has been replaced by the protecting group.

In a further embodiment the one or more acidic proton functional groups is selected from the group consisting of carboxyls, hydroxyls, primary amines, secondary amines, primary amides and secondary amides.

In a further embodiment the dialklyborane is selected from the group consisting of dicyclohexylborane, 9-borobicycloborane (9-BBN), disiamylborane, di(tert)-butyl, and diisopinocampheylborane.

In a further embodiment the functional group is reduced in less than about 5% of the product.

In a further embodiment the functional group is reduced in less than about 2% of the product.

In a further embodiment the functional group is reduced in less than about 1% of the product.

In a further embodiment the functional group is a carboxy ester group.

In a further embodiment the functional group is a methyl carboxy ester group.

In a further embodiment the functional group is a ketone group.

In a further embodiment the functional is a hydroxyl group.

In a further embodiment is provided, wherein the functional group is a nitrile group.

In a further embodiment is provided, wherein the functional group is an amino group.

In a further embodiment in step b) the mixed substituted or unsubstituted trialkylborane or a (substituted or unsubstituted alkenyl) dialkylborane is contacted with a quinone in an ether solvent.

In a further embodiment the ether solvent is tetrahydrofuran.

In a further embodiment steps a) and b) are carried out in an inert atmosphere.

In a further embodiment the inert atmosphere is nitrogen.

In a further embodiment the a unsaturated ketone is p-benzoquinone.

In a further embodiment the reaction in step a) is carried out at a temperature from about 0 to about 30 degrees centigrade.

In a further embodiment is provided, wherein the temperature of the reaction in step a) is about 20 degrees centigrade.

In a further embodiment the reaction in step b) is carried out at a temperature from about 0 to about 30 degrees centigrade.

In a further embodiment is provided, wherein the temperature of the reaction in step b) is about 20 degrees centigrade.

In a further embodiment the regioselectivity is at least 95% of the product.

In a further embodiment is provided, wherein the regioselectivity is at least 99% of the product.

In a further embodiment there is provided an substituted or unsubstituted alkyl or substituted or unsubstituted alkenyl boronic acid compound of the formula:

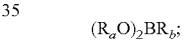

$(R_aO)_2BR_b$;

wherein $R_a$ is a hydrogen atom or an alkyl group, and $R_b$ is an alkyl or alkenyl group substituted with one or more aldehyde groups, further wherein when $R_b$ is an alkenyl group it is bound through one of the alkenyl carbons to the boron atom; and further herein when $R_b$ is an alkyl group it is bonded by a unsubstituted methylene group to the boron atom, or a trifluoroborate salt thereof.

Any of the features, in part or in whole, are combinable in any combination with any of the other paragraphs of this Summary of the Embodiments Section in part or in whole, including but not limited to aspects of methods in connection with compositions described herein or vice versa.

The present application thus provides navel compounds prepared by the methods described herein, intermediates for the synthesis of the compounds described herein, as well as methods of preparing the compounds described herein. The invention also provides compounds as described herein that are useful as intermediates for the synthesis of other useful compounds.

DETAILED DESCRIPTION

Primary alkylboronic acids and esters and corresponding potassium alkyltrifluoroborate salts are readily prepared by the hydroboration of terminal alkenes and terminal alkynes containing unprotected and protected functional groups using dialkylboranes, such as dicyclohexylborane, 9-BBN, disiamylborane and diisopinocampheylborane. The unprotected functional groups include, but are not limited to, aldehydes, ketones, carboylic esters and amides in addition to nitriles. There is little, if any, reduction of the functional group and these borane hydroborating reagents show good to excellent regioselectivity forming the primary alkyl group.

The resultant mixed alkylborane can undergo a facile two group reductive alkylation with an α,β unsaturated carbonyl compound, for example, p-benzoquinone. This transfers the secondary alkyl groups, forming a functionalized primary alkylboronic ester of the corresponding alkylhydroquinone. This ester can be converted into the corresponding potassium alkyltrifluoroborate salt. The yields from the hydroboration of the alkene to the trifluoroborate salt are often at least 80% and can be has high as 99%. In one embodiment, this is the first method to prepare functionalized boronic acids or these derivatives without protecting and &protecting the functional group. These compounds can be used in widely used coupling reactions, such as the Suzuki-Miyaura reaction.

The present application is also directed, in part, to the two-group reductive alkylation with trialkylboranes using α,β-unsaturated carbonyl compounds. The migratory aptitude for this reaction has the more substituted alkyl groups, that is, 3°>2°>1° carbons bound to the boron atom transferring faster to form the corresponding alkylated carbonyl compound.

The two-group migration allows one to remove the auxiliary secondary groups in the commonly used dialkylboranes such as 9-BBN, disiamylborane, dicyclohexylborane and diisopinocampheylborane forming an alkoxy boronic diester or boronic acid, depending on whether the reaction is quenched with water or an alcohol. This product can then be converted into the potassium trifluoroborate salt.

Primary alkyltrifluoroborate salts and the corresponding boronic acids can thus be prepared using this two-group reductive alkylation reaction.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" or to "a substituent" includes a plurality of such compounds or substituents, so that a compound X includes a plurality of compounds X or substituents. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrase "one or more" is readily understood by one of skill in the art, particularly when read in context of its usage. For example, one or more substituents on a phenyl ring refers to one to five, or one to four, for example if the phenyl ring is disubstituted.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, the composition, or the embodiment. The term about can also modify the end-points of a recited range as discuss above in this paragraph.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the molecular level, for example, to bring about a chemical reaction, or a physical change, e.g., in a solution, in a reaction mixture, including a 'neat' mixture of reactants.

An "effective amount" refers to an amount effective to bring about a recited effect, such as an amount necessary to form products in a reaction mixture. Determination of an effective amount is typically within the capacity of persons skilled in the art, especially in light of the detailed disclosure provided herein. The term "effective amount" is intended to include an amount of a compound or reagent described herein, or an amount of a combination of compounds or reagents described herein, e.g., that is effective to form products in a reaction mixture. Thus, an "effective amount" generally means an amount that provides the desired effect.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic or multicyclic aromatic ring system (a ring system with fully delocalized pi-electron system) that contain(s) one or more heteroatoms, that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline, and triazine. A heteroaryl group may be substituted or unsubstituted.

The term, "ether solvent" refers to cyclic or acyclic ethers such as tetrahydrofuran (THF), tetrahydropyran, 1,4-dioxane, and diethyl ether.

The term, "dialkylborane" refers to a borane compound wherein the boron atom is bonded to two cyclic or acyclic substituted or unsubstituted alkyl groups, which can be the same or different, further wherein the carbon bonded to the boron atom of the borane is a secondary or tertiary carbon atom. Examples include dicyclohexylborane, 9-borobicyclononane (9-BBN), disiamylborane, di(tert-butyl)borane, or diisopinocampheylborane.

The term "α,β-unsaturated carbonyl compound" refers to a compound with an aldehyde or carbonyl group directly bound to a double bond. The double bond can be part of a cyclic or acyclic alkyl group. Thus, when the compound is a ketone, there could be substituted or unsubstituted $C_{1-6}$ alkyl or cycloalkyl groups on either side of the ketone. When the carbonyl group is an aldehyde, the alkyl group is a substituted or unsubstituted $C_1$-$C_6$ alkyl or cycloalkyl groups. Examples include methyl vinyl ketone, 1,2-Benzoquinone, 1,4-Benzoquinone and Naphthaquinone. Further examples include substituted or unsubstituted benzoquinone, further wherein the quinone contains at least one vinylic proton and can optionally be substituted with one or more $C_1$-$C_6$ alkyl groups.

The term, "alcohol" when used to quench the reaction, refers to $C_1$ to $C_6$-alkyl alcohols, containing one or more hydroxy groups wherein the alkyl group includes methyl, ethyl, propyl, butyl, pentyl, hexyl or branched alkyl groups such as iso-propyl, sec-butyl, and iso-amyl.

The term "alkyl" refers to a branched or unbranched carbon chain having, for example, about 1-20 carbon atoms, and often 1-12, 1-10, 1-8, 1-6, or 1-4 carbons. Examples include, but are not limited to, methyl, ethyl, 1-propyl, 2-propyl, 1-butyl, 2-methyl-1-propyl, 2-butyl, 2-methyl-2-propyl (t-butyl), 1-pentyl, 2-pentyl, 3-pentyl, 2-methyl-2-butyl, 3-methyl-2-butyl, 3-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, dodecyl, and the like. The alkyl can be unsubstituted or substituted, for example, as described in the definition of the term "substituted" below.

The alkyl can also be optionally partially or fully unsaturated in certain embodiments. As such, the recitation of an alkyl group optionally includes both alkenyl and alkynyl groups. The alkyl can be a monovalent hydrocarbon radical, as described and exemplified above, or it can be a divalent hydrocarbon radical (i.e., an alkylene), for example, that links to other groups. In some embodiments, certain alkyl groups can be excluded from a definition. For example, in some embodiments, methyl, ethyl, propyl, butyl, or a combination thereof, can be excluded from a specific definition of alkyl in an embodiment.

The term "terminal alkenyl" refers to a monoradical branched or unbranched partially unsaturated hydrocarbon chain (i.e. a carbon-carbon, $sp^2$ double bond) preferably having from 2 to 10 carbon atoms, about 2 to 6 carbon atoms, or about 2 to 4 carbon atoms. Examples include, but are not limited to, ethylene or vinyl, cyclopentenyl, and 1-hexenyl. A terminal alkenyl group can be unsubstituted or substituted with one or more substituents defined herein except at the terminal carbon of the alkenyl bond. The terminal alkenyl must end with a methylene group at the one position of the molecule.

The term "alkenyl" refers to a monoradical branched or unbranched partially unsaturated hydrocarbon chain (i.e. a carbon-carbon, $sp^2$ double bond) preferably having from 2 to 10 carbon atoms, about 2 to 6 carbon atoms, or about 2 to 4 carbon atoms. Examples include, but are not limited to, ethylene or vinyl, allyl, cyclopentenyl, 2-hexenyl, 3-hexenyl, and 2-pentenyl. An alkenyl can be unsubstituted or substituted with one or more substituents defined herein except at the terminal carbon of the alkenyl bond.

The term "alkynyl" refers to a monoradical branched or unbranched hydrocarbon chain, having a point of complete unsaturation (i.e. a carbon-carbon, sp triple bond), typically having from 2 to 10 carbon atoms, about 2 to 6 carbon atoms, or about 2 to 4 carbon atoms. This term is exemplified by groups such as ethynyl, 1-propynyl, 2-propynyl 1-butynyl, 2-butynyl, 3-butynyl, 1-hexynyl, 2-hexynyl, 3-hexynyl, and the like. An alkynyl group can be unsubstituted or substituted and can be substituted with one or more substituents defined here.

The term "cycloalkyl" refers to cyclic alkyl groups of, for example, 3 to about 12, 3 to about 10, 3 to about 8, about 4 to about 8, or 5-6, carbon atoms having a single cyclic ring or multiple condensed rings. Cycloalkyl groups include, by way of example, single ring structures such as cyclopropyl, cyclobutyl, cyclopentyl, cyclooctyl, and the like, or multiple ring structures such as adamantyl, and the like. The cycloalkyl can be unsubstituted or substituted. The cycloalkyl group can be monovalent or divalent, and can be substituted or unsubstituted as described for alkyl groups. The cycloalkyl group can optionally include one or more sites of unsaturation, for example, the cycloalkyl group can include one or more carbon-carbon double bonds, such as, for example, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and the like. The cycloalkyl group may be substuted with one or more substituents defined herein.

A functional group refers to a substituent on another group, for example, on an alkyl group. The term functional group can be used interchangeably with the term substituent. Thus, a substituted alkyl group can contain a functional group. The term "substituted" indicates that one or more hydrogen atoms on the group indicated in the expression using "substituted" is replaced with a "substituent". The number referred to by 'one or more' can be apparent from the moiety on which the substituents reside. For example, one or more can refer to, e.g., 1, 2, 3, 4, 5, or 6; in some embodiments 1, 2, or 3; and in other embodiments 1 or 2. The substituent can be one of a selection of indicated groups, or it can be a suitable group known to those of skill in the art, provided that the substituted atom's normal valency is not exceeded, and that the substitution results in a stable compound. Suitable substituent groups can be included on substrates described herein, that do not need to be protected for the instant 2-group reductive alkylation reaction also includes examples of "non-acidic proton substituents" such as the various heavy atom chains and ring structures, include, e.g., alkyl, alkenyl, alkynyl, alkoxy, halo, haloalkyl, hydroxy, hydroxyalkyl, aryl, aroyl, (aryl)alkyl (e.g., benzyl or phenylethyl), heteroaryl, heterocycle, cycloalkyl, alkanoyl, alkoxycarbonyl, amino, alkylamino, dialkylamino, trifluoromethyl, trifluoromethoxy, trifluoromethylthio, difluoromethyl, acylamino, nitro, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxyl amine, hydroxyl (alkyl)amine, and cyano. Additionally, suitable substituent groups can be, e.g., —X, —R, —B(OH)$_2$, —B(OR)$_2$, —O$^-$, —OR, —SR, —S$^-$, —NR$_2$, —NR$_3$, =NR, —CX$_3$, —CN, —OCN, —SCN, —N=C=O, —NCS, —NO, —NO$_2$, =N$_2$, —N$_3$, —NC(=O)R, —C(=O)R, —C(=O)NRR, —S(=O)$_2$O$^-$, —S(=O)$_2$R, —OS(=O)$_2$OR, —S(=O)$_2$NR, —S(=O)R, —OP(=O)O$_2$RR, —P(=O)O$_2$RR, —P(=O)(O$^-$)$_2$, , —C(=O)H, —C(=O)X, —C(S)R, —C(O)OR, —C(O)O$^-$, —C(S)OR, —C(O)SR, —C(S)SR, —C(O)NRR, —C(S)NRR, or —C(NR)NRR, where each X is independently a halogen ("halo"): F, Cl Br, or I; and each R is independently alkyl, aryl, (aryl)alkyl (e.g., benzyl), heteroaryl, (heteroaryl)alkyl, heterocycle, heterocycle (alkyl), or a protecting group. As would be readily understood by one skilled in the art, when a substituent is keto (=O) or thioxo (=S), or the like, then two hydrogen atoms on the substituted atom are replaced. In some embodiments, one or more of the substituents above are excluded from the group of potential values for substituents on the substituted group.

The term "functional groups containing one or more acidic protons" are groups that need to be protected with protecting groups are Bronsted acids when used in the instant 2-group reductive alkylation reaction with pKa of about 18 or lower. Examples of such include —OH, —SH, —NH$_2$, —CONH$_2$, —CONHR, —COOH, —NH$_2$OH, —SO$_3$H, and —P(=O)(OH)$_2$.

Where the compounds disclosed herein have at least one chiral center, they may exist as individual enantiomers and diastereomers or as mixtures of such isomers, including racemates. Separation of the individual isomers or selective synthesis of the individual isomers is accomplished by application of various methods which are well known to practitioners in the art. Unless otherwise indicated, all such isomers and mixtures thereof are included in the scope of the compounds disclosed herein. Furthermore, compounds disclosed herein may exist in one or more crystalline or amorphous forms. Unless otherwise indicated, all such forms are included in the scope of the compounds disclosed herein including any polymorphic forms. In addition, some of the compounds disclosed herein may form solvates with water (i.e., hydrates) or common organic solvents. Unless otherwise indicated, such solvates are included in the scope of the compounds disclosed herein.

The skilled artisan will recognize that some structures described herein may be resonance forms or tautomers of compounds that may he fairly represented by other chemical structures, even when kinetically; the artisan recognizes that such structures may only represent a very small portion of a sample of such compound(s). Such compounds are considered within the scope of the structures depicted, though such resonance forms or tautomers are not represented herein.

The term "protecting group" as used herein refers to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis,* 3rd Ed. John Wiley & Sons, 1999, and in J. F. W. McOmie, *Protective Groups in Organic Chemistry* Plenum Press, 1973, both of which are hereby incorporated by reference. The protecting group moiety may be chosen in such a way, that they are stable to the reaction conditions applied and readily removed at a convenient stage using methodology known from the art. A non-limiting list of protecting groups include benzyl; substituted benzyl; alkylcarbonyls (e.g., t-butoxycarbonyl (BOC)); arylalkylcarbonyls (e.g., benzyloxycarbonyl, benzoyl); substituted methyl ether (e.g. methoxymethyl ether); substituted ethyl ether; a substituted benzyl ether; tetrahydropyranyl ether; silyl ethers (e.g., trimethylsilyl, triethylsilyl, triisopropylsilyl, t-butyldimethylsilyl, or t-butyldiphenyisilyl), esters (e.g. benzoate ester); carbonates (e.g. tnethoxyraethylcarbonate); acyclic ketal (e.g. dimethyl acetal); cyclic ketals (e.g., 1,3-dioxane or 1,3-dioxolanes); and cyclic dithioketals (e.g., 1,3-dithiane or 1,3-dithiolane), alkylsilyls (e.g., tris(trimethyl)silyl, t-butyldimethylsilyl), levulinyl, and monomethoxytrityl.

General Preparatory Methods

The two-group reductive alkylation reaction described herein can use any of the applicable techniques of organic synthesis and the related arts. Many such techniques are well known to the skilled artisan. Accordingly, many of the known techniques are elaborated in, for example, *Compendium of Organic Synthetic Methods* (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6, Michael B. Smith; as well as March, J., *Advanced Organic Chemistry, Third Edition*, (John Wiley & Sons, New York, 1985); *Comprehensive Organic Synthesis. Selectivity, Strategy & Efficiency in Modern Organic Chemistry. In 9 Volumes*, Barry M. Trost, Editor-in-Chief (Pergamon Press, New York, 1993 printing); *Advanced Organic Chemistry, Part B: Reactions and Synthesis. Second Edition*, Cary and Sundberg (1983); *Protecting Groups in Organic Synthesis, Second Edition*, Greene, T. W., and Wutz, P. G. M., John Wiley & Sons, New York; and *Comprehensive Organic Transformations*, Larock, R. C., Second Edition, John Wiley & Sons, New York (1999).

Those skilled in the art will be able to recognize modifications of the disclosed syntheses and to devise alternate routes based on the disclosures herein; all such modifications and alternate routes are within the scope of the claims.

Applications of the Methods and Reaction Products Described Herein

The alkylboronate esters and trifluoroborate salts generated in the reactions described herein can be readily converted to primary alcohols and to primary alkylarenes using standard synthetic transformations. The primary alkylboronate esters can also be further derivatized to provide scaffolds for combinatorial libraries. For example, boronic acids or esters can be transformed into myriad functional groups including aryl or vinyl groups via Suzuki-Miyaura couplings (Miyaura and Suzuki, *Chem. Rev.* 95: 2457-2483 (1995); Suzuki, *J. Organomer. Chem.* 576: 147-168 (1999); Miyaura, In *Advances in Metal-Organic Chemistry*, Liebeskind, Ed.: JAI; London, VOL 6, pp. 187-243 (1998); see also *Metal-catalyzed Cross-coupling Reactions;* Diederich and Stang, Eds.; Wiley: Wienheim, 1998). Organoboron compounds can also undergo efficient transmetallation to palladium and other transition metals followed by reactions with aryl halides and the like, or coupling under oxidative conditions, to provide various synthetically valuable compounds. Numerous examples of such reactions are described in standard references texts such as *March's Advanced Organic Chemistry: Reactions, Mechanisms, and Structure, 5th Ed.* (M. B. Smith and J. March, John Wiley & Sons, New York, 2001).

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

Some embodiments provide methods for boronic derivatives to undergo both 1,4-additions to conjugated enones as well as 1,2-addition to aldehydes. Some embodiments provide methods for the Mizoroki-Heck catalyzed cross coupling reactions of aryl and vinylboronic derivatives. Some embodiments provide methods for the Boron-Mannich (Petasis) reaction. Some embodiments provide methods for the formation of carbon-heteroatom bonds. Some embodiments provide methods for the Chan-Lam coupling reaction.

EXAMPLES

Additional embodiments are disclosed in further detail in the following examples, which are not in any way intended to limit the scope of the claims.

All of the alkyltrifluoroborate salts are fully characterized by high field NMR. The spectra collected included 1-D $^{11}$B, $^{19}$F, $^{1}$H and $^{13}$C as well as DEPT and 2-D NMR experiments on COSY and HSQC. The spectra were run on Varian VNMRS 400, NOVA 500 and VNMRS 600 MHz NMR spectrometers using indirect detection pulse field gradient probes.

Example 1

Preparations of Functionalized Potassium Primary Alkyltrifluoroborate Salts via Hydroboration of a Terminal or 2-Alkyl-1-alkene and Dicyclohexylborane, 9-Borabicyclo[3.3.1]nonane (9-BBN), Bis(3-methyl-2-butyl)borane disiamylborane) or Diisopinocampheylborane (Ipc$_2$BH)

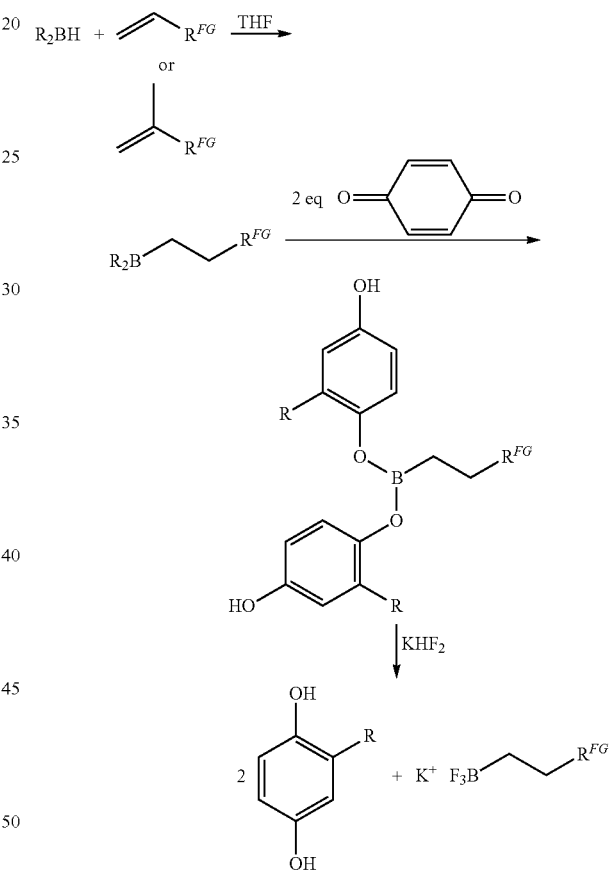

The same flask, described below, used to prepare the dicyclohexylborane or diisopinocatnpheylborane, was used for the hydroboration of the functionalized terminal alkene. Tetrahydrofuran was added to the solid dialkylborane. In the cases of disiamylborane or 9-BBN, a known volume of standardized borane-THF solution was added to a septum capped side-armed round bottom and fitted with a magnetic stirring bar and gas-inlet adapter. The functionalized alkene was added to the borane solution, 1.1 equiv, and the reactions were monitored by $^{11}$B NMR. Most reactions were complete within 1 hour at room temperature (~22° C.).

The percent of the boronic derivatives at 53 ppm versus the amount of the trialkylborane can be used to determine the amount of reduced functional group versus amount of hydroboration. The regioselectivity can also be determined by a variety of techniques. The 1-alkyl group is shifted upfield to a greater extent than the 2-alkyl groups. One can determine the regioselectivity of the hydroboration of the functionalized alkene based on the percentage of these two shifted species. It is known that functional groups affect the regioselectivity in hydroboration reactions.

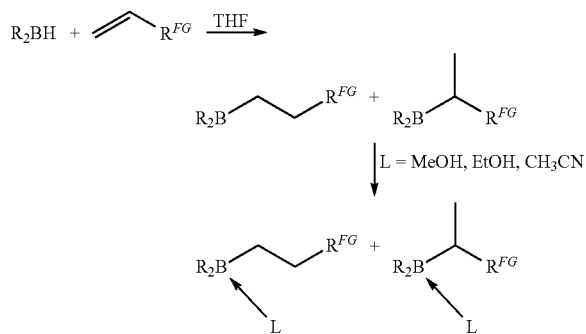

A 1.0 molar solution of freshly sublimed p-benzoquinone in THF is slowly added dropwise to the THF solution of the mixed trialkylborane formed above. There was an immediate loss of the intense quinone yellow color on addition. This color began to persist after 1.8 equiv of the quinone had been added.

A THF solution containing one equivalent of alkylboronic ester was hydrolyzed with four equivalents of $H_2O$ for 30 minutes. Approximately ¾ of the THF was removed under vacuum and the reaction flask was filled with $N_2$. A serum vial containing a small magnetic stir bar was charged with 2.5 equivalents of capped with a septum, and thoroughly flushed with $N_2$. Boiled water (2.5 mL/g $KHF_2$) was added to the serum vial with the aid of a syringe and stirred until the salt dissolved. The $KHF_2$ solution was added dropwise with the aid of a double-ended needle to the THF solution of boronic acid and stirred for 30 minutes. Water and THF were carefully removed under vacuum until the solids are dry. The gas-inlet valve was removed from the reaction apparatus and the solids were transferred to an Erlenmeyer flask with the aid of acetone. The acetone was heated to dissolve the organics, which were then filtered through a pad of powdered cellulose filter aid on a Buchner funnel. The acetone was removed on a rotary evaporator; the remaining solids were triturated with ethyl ether, filtered on a Buchner funnel and washed with ether. The ether solution contained the alkylhydroquinone based on the auxiliary group used for the hydroboration.

Characterization: The $^{11}B$ NMR spectrum showed a single broad quartet resonance signal 4-7 ppm, free of any other boron materials. The $^{19}F$ spectrum also showed a single resonance signal in the region −135-140 ppm. This signal is indicative an alkyltrifluoroborate salt, and there was a lack of any signals that can be attributed to the hydrogen difluoride, potassium fluoride or tetrafluoroborate. The proton NMR spectrum is consistent with structure of the alky group and the hydrogens attached to the α-carbon are shifted upfield, 0.1-0.2 ppm, observed as a broad multiplet. The $^{13}C$ NMR spectrum is in agreement with the expected chemical shifts of the structure using chemical shifts shielding values based on known alkyltrifluoroborate salts. In general, formed compounds are fully characterized and assigned using $^1H$, $^{13}C$, COSY and HSQC experiments. The NMR spectra also indicate a pure compound with impurities of less than 1%.

Example 2

Reductive Alkylation of 1,4-Benzoquinone Using Mixed (Methylated) Organoboranes

The reaction vessel was charged with $(hex)_2BMe$ (3 mL, 2.59 mmol); to which, 3 mL of THF was added as a diluent. The charged reaction vessel was then placed in a room temperature water bath. Approximately two equivalents of p-benzoquinone (0.528 g, 4.888 mmol) were weighed out and dissolved in 5.1 mL THF, which gave a volume of 5.7 mL of ~1M solution. The quinone solution was introduced to the reaction mixture by dropwise addition at a consistent, slow rate during which the quinone color changed as alkylation proceeded. Approximately 4.5 hours after the quinone addition was initiated, the color was extinguished. The general procedure for reductive alkylation of benzoquinone by mixed organoborane is below.

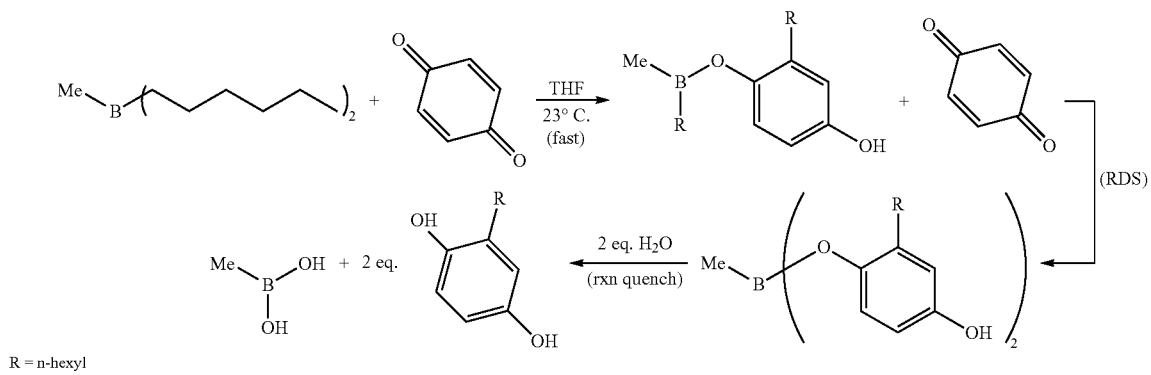

A 0.5 mL (~0.1036 mmol) aliquot of the borane solution was removed for $^{11}B$ NMR spectroscopic analysis. The spectroscopy revealed a resonance signal at 53.8 ppm with an estimated integrated product area of 26.93%, to which was assigned the mixed alkyl borinic phenolate ester, (hex)BMe(hexHQ). The mentioned signal was occluded by a signal at 53 ppm with an estimated area of 5.75%, to which was assigned the previously seen bonnie species; most probably, (hex)BMe(Ohex). Further upfield were seen two overlapping signals at 29.9 and 28.4 ppm, respectively. The signal at 29.9 ppm had an estimated area of 42.9%. Two borane species were attributed to this signal; notably, the alkylated boronic phenolate ester (~40.5%). and the previously seen boronic species (~2.4%).

After the foregoing analysis, the reaction was quenched by the addition of 0.085 mL $N_2$ purged DI water (~4.68 mmol), while the reaction solution stirred for 15 minutes. in this manner the alkylated quinone was liberated from the borane, and the air stable boronic acid was formed.

Example 3

Reductive Alkylation of 1,4-Benzoquinone Using Mixed (Nonmethylated) Trialkylboranes The reaction diagram for reductive alkylation of 1,4-benzoquinone by mixed alkylborane is below.

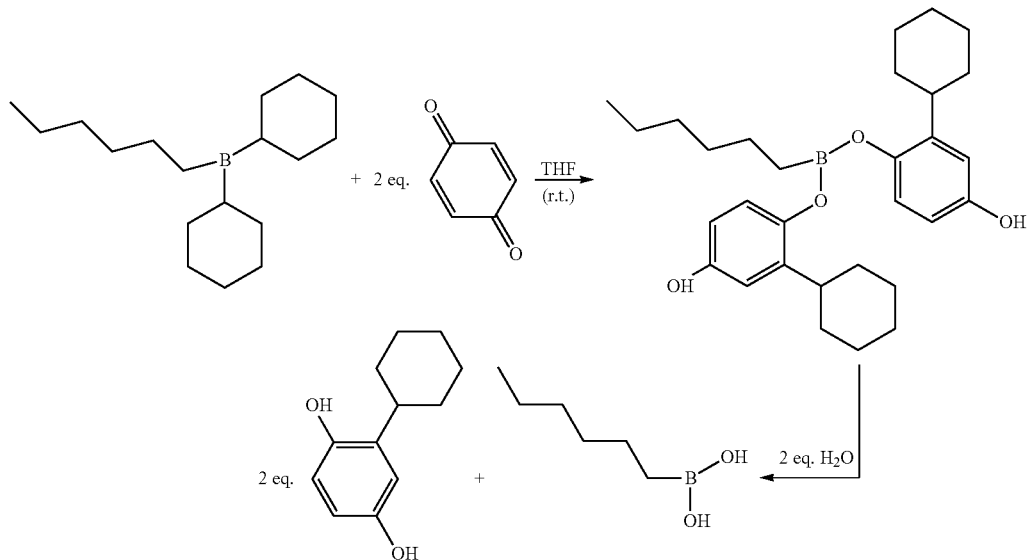

Reductive alkylation in THF: A reaction vessel was placed in a room temperature water-bath, and 3 mL THF was added to the vessel. The reaction vessel was charged with 1 mL (~2.4 mmol) of $(Cy)_2Bhex$. Benzoquinone (0.2594 g; 2.4 mmol) was dissolved in 2.6 mL THF. A dropwise addition of the first equivalent of benzoquinone was performed over approximately two minutes.

A 0.5 mL aliquot of the reaction mixture was removed for $^{11}B$ NMR analysis. Within 15 minutes of the benzoquinone's addition, spectroscopy showed a signal at 83 ppm with an area of 7.5%, attributed the initial borane, $(Cy)_2Bhex$. The dominant signal was seen at 53.6 ppm with an area of 87.4%, and was attributed alkylated hydroquinone bonnie ester, and the bonnie ester side-product of the initial borane. A third signal was observed at 31 ppm with an area of 5.1%, to which was attributed alkylated hydroquinone boronic ester.

A second equivalent of benzoquinone (0.2396 g; 2.2 mmol) was dissolved in 2.4 mL THF then added dropwise over a two-minute period to the reaction mixture.

Another 0.5 mL aliquot was removed from the reaction vessel for $^{11}B$ NMR analysis. Less than 15 minutes after the benzoquinone addition was complete, $^{11}B$ NMR spectroscopy showed a single signal at 27.9 ppm, which indicated all of the borane had been converted to alkylated hydroquinone boronic ester. An addition of deionized water (~0.09 mL; ~5 mmol) hydrolyzed the boronic ester and liberated alkylated hydroquinone.

Reductive Alkylation in $Et_2O$/THF solution: The foregoing experiment was modified by substitution of $Et_2O$ for some of the THF in the reaction vessel, and by making the two equivalent addition of benzoquinone without an intervening $^{11}B$ NMR analysis. The reaction vessel was placed in a room temperature water-bath, and 3 mL $Et_2O$ was placed in the vessel. The reaction vessel was then charged with 0.5 mL (~1.2 mmol) of the $(Cy)_2Bhex$. Two equivalents of benzoquinone was measured (0.2594 g; 2.4 mmol) and dissolved in 2.6 mL THF. Dropwise addition of the benzoquinone over a period of 90-120 seconds was performed.

A 0.5 mL aliquot of the borane solution was removed for $^{11}B$ NMR analysis. Notably, the borane solution was clear of any color within 1.5 minutes of the benzoquinone's addition.

The spectroscopy showed a signal at 52 ppm with an area of 24.9%, to which was attributed the alkylated hydroquinone bonnie ester and the unidentified bonnie species side-product of the initial borane. The dominant signal was observed at 30.1 ppm with an area of 75.1%, to which was attributed the alkylated hydroquinone boronic ester. Further $^{11}B$ NMR analyses were made for another 48 hours. The final analysis showed a signal at 53 ppm with an area of 2.1%, attributed to the bonnie ester. The dominant signal was seen at 31.2 ppm with an area of 94.7% attributed to the boronic ester.

The boronic ester was hydrolyzed by addition of deionized water (~0.09 mL; ~5 mmol) to quench the reaction and to liberate the alkylated hydroquinone moiety.

Reductive Alkylation in Pentane/THF solution. The foregoing experiment was modified by substitution of pentane for some of the THF in the reaction vessel, and by making the two equivalent addition of benzoquinone without an intervening $^{11}B$ NMR analysis. The reaction vessel was placed in a room temperature water-bath, and 3 mL pentane was placed in the vessel. $(Cy)_2Bhex$ was used, and the reaction vessel was charged with 0.4 mL (~0.96 mmol) of the borane. Solid benzoquinone was measured (0.2077 g;

1.92 mmol) and dissolved in 2.1 mL THF. Dropwise addition of the benzoquinone was completed within two minutes.

A 0.5 mL aliquot of the reaction mixture was removed for $^{11}$B NMR analysis. Notably, the borane solution was clear of any observable color within 15 minutes of the quinones addition, the spectroscopy showed a signal at 52 ppm with an area of 26.8%, to which was attributed the alkylated hydroquinone bonnie ester and the bonnie species side-product of the initial borane. The dominant signal was observed at 30.2 ppm with an area of 73.2%, to which was attributed the alkylated hydroquinone boronic ester.

The final NMR analysis was performed 25 hours after the benzoquinone addition was completed. A signal was seen at 53 ppm with an area of 3.1%, to which a bonnie species was attributed; also seen was the dominant signal at 30.9 ppm with an area of 96.9%, attributed to the alkylated hydroquinone boronic species. The boronic ester was hydrolyzed by addition of deionized water (~0.04 mL; ~2 mmol) to quench the reaction and to liberate the alkylated hydroquinone moiety.

Example 3

Separation and Characterization of n-Hexyl-Boronic Acid

Hydrolysis of the borane intermediate liberated alkylated hydroquinone and formed n-hexyl-boronic acid. A 0.2 mL aliquot of the boronic acid was removed and 0.5 mL of CDCl$_3$ was added for performing $^1$H and $^{11}$B NMR analyses. The $^{11}$B NMR spectroscopy showed one signal at 32.2 ppm, likely the n-hexyl-boronic acid. Analysis of the $^1$H NMR spectroscopy revealed 0.71 ppm (t, J=8.2 Hz, 2 H's); 0.87 ppm (t, J=7.3 Hz, 3 H's); and a series of unresolved signals in the range of 1.22-1.50 ppm, likely the protons of the interior carbons of the boronic acid's hexyl substituent.

Example 4

Synthesis of Potassium 5-oxohexyltrifluoroborate

Dicyclohexylborane was prepared in a THF solution using air-sensitive techniques working under a nitrogen atmosphere. The 50 mL reaction flask with a side-arm, stir bar, and gas-inlet adaptor were oven dried, assembled hot, the side-arm covered with a septum and cooled under a stream of dry nitrogen. The reaction flask was cooled to 0° C. in an ice-bath. Anhydrous THF, 4 mL was added to the flask with a syringe and stirred with cooling to 0° C. Next, neat borane dimethylsulfide was added, 5 mmol, 0.5 mL. After this solution had cooled, 10 mmol of cyclohexene was added dropwise with stirring. A white precipitate formed within 10 minutes. The mixture was stirred for 1.5 to 2 hours to ensure a complete reaction. One equivalent of 5-hexen-2-one, 5 mmol, 0.56 g, was added dropwise to the cooled mixture. After approximately 5 min, the solid dicyclohexylborane dissolved forming a homogeneous solution. A solution of p-benoquinone in THF, 10 mmol, 1.08 g in 10 mL THF, was added dropwise to the alkyldicyclohexylborane solution until the yellow color of the quinone remained a persistent light yellow color indicating complete reaction. The reaction solution was stirred for an additional 15 min. Approximately one-half of the volatiles were removed under reduced pressure then an aqueous solution of potassium hydrogen difluoride, 2.5 eq, 12.5 mmol, ca. 3.0 M, was added to the reaction solution and stirred for 15 min. The volatiles were removed under vacuum with mild heating to yield a dry solid. Diethyl ether was added to the solid material forming a slurry which was vacuum filtered on a Büchner filter, washed with 50 mL of ether yielding a white precipitate. This material was dissolved in 50 mL of hot acetone, filtered to remove the potassium hydrogen difluoride. The filtrate was concentrated on a rotovap to give the desired Potassium 5-oxohexyltrifluoroborate as a white precipitate (0.71 g, 3.45 mmol, 69%). The boron NMR spectra show a quartet at 5.19 ppm J=61 hz. The proton NMR showed the following resonances: (600 MHz, acetone d$_6$): 2.34 (d, J=7.2 Hz, 2H), 2.05 (s, 3 Hz), 1.49 (q, J=7.8 Hz, 2H), 1.24 (m, J=7.8 Hz, 2H), 0.12 (d/d, J=8.4, 7.2 Hz, 2H). $^{13}$C NMR (150.74 MHz, acetone d$_6$): 208.21, 205.15, 43.72, 29.27, 29.14, 29.01, 28.88, 28.756, 28.63, 28.50, 27.61, 25.40. $^{19}$F NMR (470.41 MHz, acetone d$_6$): −140.83 ppm.

Example 5

Synthesis of Potassium 3-trifluoroborato-1-propanol, (potassium trifluoro(3-hydroxypropyl)borate)

Dicyclohexylborane was prepared in a THF solution using air-sensitive techniques working under a nitrogen atmosphere. The 50 mL reaction flask with a side-arm, stir bar, and gas-inlet adaptor were oven dried, assembled hot, the side-arm covered with a septum and cooled under a stream of dry nitrogen. The reaction flask was cooled to 0° C. in an ice-bath. Anhydrous THF, 4 mL was added to the flask with a syringe and stirred with cooling to 0° C. Next, neat borane dimethylsulfide was added, 5 mmol, 0.5 mL. After this solution had cooled, 10 mmol of cyclohexene was added dropwise with stirring. A white precipitate formed within 10 minutes. The mixture was stirred for 1.5 to 2 hours to ensure a complete reaction. One-third equivalent of triallylborate, 1.67 mmol, 0.304 g, was added dropwise to the cooled borane mixture. After approximately 5 rain, the solid dicyclohexylborane dissolved forming a homogeneous solution. A solution of p-benoquinone in THF, 10 mmol, 1.08 g in 10 mL THF, was added dropwise to the alkyldicyclohexylborane solution until the yellow color of the quinone remained a persistent light yellow color indicating complete reaction. The reaction solution was stirred for an additional 15 min. Approximately one-half of the volatiles were removed under reduced pressure then an aqueous solution of potassium hydrogen difluoride, 3.5 eq, 17.5 mmol, ca. 3.0 M, was added to the reaction solution and stirred for 15 min. The volatiles were removed under vacuum with mild heating to yield a dry solid. Diethyl ether was added to the solid material forming a slurry which was vacuum filtered on a Büchner filter, washed with 50 mL of ether yielding a white precipitate. This material was dissolved in 50 mL of hot acetone, littered to remove the potassium hydrogen difluoride. The filtrate was concentrated on a rotovap to give the desired Potassium 3-trifluoroborato-1-propanol as a white precipitate (0.60 g, 3.65 mmol, 73%). The boron NMR spectra show a multiplet at 4.16 ppm. The proton NMR showed the following resonances: (600 MHz, acetone d$_6$): 3.36 (t, J=7.2 Hz), 1.28 (m, 2H), 0.25 (m, 2H). $^{13}$C NMR (150.74 MHz, acetone d$_6$): 66.45, 28.9, 16.4. $^{19}$F NMR (470.41 MHz, acetone d$_6$): −137.2 ppm.

Example 6

Synthesis of Potassium 5-trifluoroboratopentaonate Methyl Ester

Dicyclohexylborane was prepared in a THF solution using air-sensitive techniques working under a nitrogen atmosphere. The 50 mL reaction flask with a side-arm, stir bar, and gas-inlet adaptor were oven dried, assembled hot, the side-arm covered with a septum and cooled under a stream of dry nitrogen. The reaction flask was cooled to 0° C. in an ice-bath. Anhydrous THF, 4 mL was added to the flask with a. syringe and stirred with cooling to 0° C. Next, neat borane dimethylsulfide was added. 5 mmol, 0.5 mL. After this solution had cooled. 10 mmol of cyclohexene was added dropwise with stirring. A white precipitate formed within 10 minutes. The mixture was stirred for 1.5 to 2 hours to ensure a complete reaction. One equivalent of methyl 4-pentenoate, 5.01 mmol, 0.304 g, was added dropwise to the cooled borane mixture. After approximately 5 min, the solid dicyclohexylborane dissolved forming a homogeneous solution. A solution of p-benoquinone in THF, 10 mmol, 1.08 g in 10 mL THF, was added dropwise to the alkyldicyclohexylborane solution until the yellow color of the quinone remained a persistent light yellow color indicating complete reaction. The reaction solution was stirred for an additional 15 min. Approximately one-half of the volatiles were removed under reduced pressure then an aqueous solution of potassium hydrogen difluoride, 2.5 eq, 12.5 mmol, ca. 3.0 M, was added to the reaction solution and stirred for 15 min. The volatiles were removed under vacuum with mild heating to yield a dry solid. Diethyl ether was added to the solid material forming a slurry which was vacuum filtered on a Büchner filter, washed with 50 mL of ether yielding a white precipitate, This material was dissolved in 50 mL of hat acetone, filtered to remove the potassium hydrogen difluoride. The filtrate was concentrated on a rotovap to give the desired Potassium 5-trifluoroboboratopentaonate methyl ester as a white precipitate (0.59 g, 2.66 mmol, 53%). The boron MIR spectra show a broad signal at 5.84. The proton NMR showed the following resonances: (400 MHz, acetone $d_6$): 3.59 (2, 3H), 2.22 (t, J=7.6 Hz, 2H), 1.54 (pentet, J=7.6 Hz, 2H), 1.27 (m, 2H), 0.14 (septet, J=7.3 Hz, 2H). $^{13}$C NMR (100.50 MHz, acetone $d_6$): 174.96, 51.36, 34.98, 29.44, 26.2, 19.7. $^{19}$F NMR (376.33 MHz, acetone ($1_6$): −140.9 ppm.

Example 7

Synthesis of Potassium (1E)-1-hexen-1-trifluoroborate

Dicyclohexylborane was prepared in a THF solution using air-sensitive techniques working under a nitrogen atmosphere. The 0 mL reaction flask with a side-arm, stir bar, and gas-inlet adaptor were oven dried, assembled hot, the side-arm covered with a septum and cooled under a stream of dry nitrogen. The reaction flask was cooled to 0° C. in an ice-bath. Anhydrous THF, 4 mL was added to the flask with a syringe and stirred with cooling to 0° C. Next, neat borane dimethylsulfide was added, 5 mmol, 0.5 mL. After this solution had cooled, 10 mmol of cyclohexene was added dropwise with stirring. A white precipitate formed within 10 minutes. The mixture was stirred for 1.5 to 2 hours to ensure a complete reaction. One equivalent of 1-hexyne, 5.01 mmol, 0.41 g, was added dropwise to the cooled borane mixture. After approximately 5 min, the solid dicyclohexylborane dissolved forming a homogeneous solution. A solution of p-benoquinone in THF, 10 mmol, 1.08 g in 10 mL THF, was added dropwise to the alkyldicyclohexylborane solution until the yellow color of the quinone remained a persistent light yellow color indicating complete reaction. The reaction solution was stirred for an additional 15 min. Approximately one-half of the volatiles were removed under reduced pressure then an aqueous solution of potassium hydrogen difluoride, 2.5 eq, 12.5 mmol, ca. 3.0 M, was added to the reaction solution and stirred for 15 min. The volatiles were removed under vacuum with mild heating to yield a dry solid. Diethyl ether was added to the solid material forming a slurry which was vacuum filtered on a Büchner filter, washed with 50 mL of ether yielding a white precipitate. This material was dissolved in 50 mL of hot acetone, filtered to remove the potassium hydrogen difluoride. The filtrate was concentrated on a rotovap to give Potassium (1E)-1-hexen-1-trifluoroborate as a white precipitate (0.86 g, 4,51 mmol, 90%). The boron NMR spectra show a broad quartet signal at 2.8 ppm. The proton NMR showed the following resonances: (400 MHz, acetone $d_6$): 5.68 (m, 1H), 5.38 (m, 1H), 1.95 (m, 2H), 1.29 (m, 4H), 0.85 (t, J=7.5 Hz, 3H). $^{13}$C NMR (100.50 MHz, acetone $d_6$): 135.21, 36.47, 32.95, 23.16, 14.44. $^{19}$F NMR (376.33 MHz, acetone $d_6$): −141.0 ppm.

Example 8

Synthesis of Potassium p-menthan-2-one-9-trifluoroborate

Dicyclohexylborane was prepared in a THF solution using air-sensitive techniques working under a nitrogen atmosphere. The 0 mL reaction flask with a side-arm, stir bar, and gas-inlet adaptor were oven dried, assembled hot, the side-arm covered with a septum and cooled under a stream of dry nitrogen. The reaction flask was cooled to 0° C. in an ice-bath. Anhydrous THF, 4 mL was added to the flask with a syringe and stirred with cooling to 0° C. Next, neat borane dimethylsulfide was added, 5 mmol, 0.5 mL. After this solution had cooled, 10 mmol of cyclohexene was added dropwise with stirring. A white precipitate formed within 10 minutes. The mixture was stirred for 1.5 to 2 hours to ensure a complete reaction. One equivalent of dihydrocarvone, 4.98 mmol, 1.14 g, was added dropwise to the cooled borane mixture. After approximately 5 min, the solid dicyclohexylborane dissolved forming a homogeneous solution. A solution of p-benoquinone in THF, 10 mmol, 1.08 g in 10 mL THF, was added dropwise to the alkyldicyclohexylborane solution until the yellow color of the quinone remained a persistent light yellow color indicating complete reaction. The reaction solution was stirred for an additional 15 min. Approximately one-half of the volatiles were removed under reduced pressure then an aqueous solution of potassium hydrogen difluoride, 2.5 eq, 12.5 mmol, ca. 3.0 M, was added to the reaction solution and stirred for 15 min. The volatiles were removed under vacuum with mild heating to yield a dry solid. Diethyl ether was added to the solid material forming a slurry which was vacuum filtered on a Büchner filter, washed with 50 mL of ether yielding a white precipitate. his material was dissolved in 50 mL of hot acetone, filtered to remove the potassium hydrogen difluoride. The filtrate was concentrated on a rotovap to give Potassium p-menthan-2-one-9-trifluoroborate as a white precipitate (0.80 g, 3.07 mmol, 62%). The boron NMR spectra show a broad quartet signal at 4.6 ppm. The proton NMR showed the following resonances: (400 MHz, acetone $d_6$): 2.34 (m, 1H), 2.15 (m, 2H), 1.80 (m, 1H), 1.78 (m, 1H), 1.60 (m, 4H), 0.92 (d, J=7.3, 3H), 0.29 (m, 1H), −0.01 (m, 1H). $^{19}$F NMR (376.33 MHz, acetone $d_6$): −135.2 ppm.

Example 9

Synthesis of Potassium 4-trifluoroboratobutyronitrile

The above procedure was used to prepare the mixed dicyclohexylalkylborane then reacted with two equivalents of p-benzoquinone and converted to the Potassium 4-trifluoroboratobutyronitrile which was isolated as a white precipitate (0.72 g, 4.12 mmol, 82%). The boron NMR spectra show a broad quartet signal at 1.82 ppm. The proton NMR showed the following resonances: (400 MHz, acetone $d_6$): 2.30 (t, J=7.4 Hz, 2H), 1.45 (pentet, J=7/5 Hz, 2H), 0.09 (m, 2H). $^{13}$C NMR (100.50 MHz, acetone $d_6$): 121.68, 22.10, 19,11. $^{19}$F NMR (376.33 MHz, DMSO $d_6$): −137.5 ppm.

Example 10

Synthesis of Potassium 3-trifluoroboratopropyl Acetate

The above procedure was used to prepare the mixed dicyclohexylalkylborane then reacted with two equivalents of p-benzoquinone and converted to the of Potassium 3-trifluoroboratopropyl acetate which was isolated as a white precipitate (0.82 g, 3,92 mmol, 79%). The boron NMR spectra show a broad quartet signal at 4.63 ppm. The proton NMR showed the following resonances: (400 MHz, DMSO $d_6$): 3.86 (t, J=7.4 Hz, 3H), 1.95 (s, 3H), 1.41 (pentet, J=7.4 Hz, 2H), −0.08 (in, 2H), $^{13}$C NMR (100.50 MHz, DMSO $d_6$): 170.36, 67.40, 24.86, 18.4. $^{19}$F NMR (376.33 MHz, DMSO $d_6$): −137.3 ppm.

Example 11

Synthesis of Potassium N-Acetyl(3-trifluoroboratopropypl)amino 2,2-dimethylprionate The above procedure was used to prepare the mixed dicyclohexylalkylborane then reacted with two equivalents of p-benzoquinone and converted to the Potassium N-Acetyl (3-trifluoroboratopropyl)amino 2,2-dimethylprionate which was isolated as a white precipitate (1.31 g, 4.25 mmol, 85%). The boron NMR spectra show a broad quartet signal at 5,32 ppm. The proton NMR showed the following resonances: (400 MHz, acetone $d_6$): 3.57 (t, J=7.4 Hz, 2H), 2.35 (s, 3H), 1.52 (s, 9H), 1.44 (pentet, J=7.6 Hz, 2H), 0.10 (m, 2H). $^{13}$C NMR (100.50 MHz, acetone $d_6$); 173.10, 154.57, 82.86, 47.99, 28,25, 27.13, 25.57, 17.7 (b). $^{19}$F NMR (376.33 MHz, acetone ($1_6$): −140.8 ppm.

While the disclosure has been illustrated and described in detail in the drawings and foregoing description, such illustration and description are to be considered illustrative or exemplary and not restrictive. The disclosure is not limited to the disclosed embodiments. Variations to the disclosed embodiments can be understood and effected by those skilled in the art in practicing the claimed disclosure, from a study of the drawings, the disclosure and the appended claims.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not he taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not he construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean al least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

The following numbered items provide further disclosure forming part of the present application.
1. A method for synthesizing an substituted or unsubstituted alkylboronic acid or substituted or unsubstituted alkenyl boronic acid, comprising:
   a) contacting a dialkylborane with at least one compound selected from the group consisting of a substituted or unsubstituted terminal alkene and a substituted or unsubstituted alkyne to provide a mixed substituted or unsubstituted trialkylborane or a (substituted or unsubstituted alkenyl) dialkylborane;
   b) contacting the mixed substituted or unsubstituted trialkylborane or the (substituted or unsubstituted alkenyl)dialkylborane of step a) with at least two equivalents of an $\alpha,\beta$-unsaturated carbonyl compound to provide a substituted or unsubstituted alkyl boronate diester or a substituted or unsubstituted alkenyl boronate diester; and
   c) contacting either water or an alcohol with the boronate diester from step b) to quench the reaction and to yield a corresponding boronic acid product or a corresponding alkoxyboronate diester product.
2. The method 1, wherein after step c) the boronic acid or boronate diester product is further reacted with potassium hydrogen difluoride to yield a substituted or unsubstituted alkyltrifluoroborate salt or a substituted or unsubstituted alkenyltrifluoroborate salt.
3. The method of 1 or 2, wherein the substituted or unsubstituted terminal alkene or the substituted or unsubstituted alkyne is substituted with a functional group and the functional group is unprotected when it is contacted with the dialkylborane.
4. The method of 1, , 2 or 3, wherein the functional group is selected from the group of non-acidic proton substituents.
5. The method of 1, 2, 3 or 4, wherein the non-acidic proton substituents are selected from the group consisting of one or more aldehydes, ketones, carboxy esters, nitriles, lactams, lactones, and tertiary amides.
6. The method of 1, wherein the substituted or unsubstituted terminal alkene, or the substituted or unsubstituted alkyne, is substituted with a functional group containing one or more acidic protons and these one or more functional groups are also bonded to a protecting group such that the acidic proton on the functional group has been replaced by the protecting group.
7. The method of 1 or 6, wherein the one or more acidic proton functional groups is selected from the group consisting of carboxyls, hydroxyls, primary amines, secondary amines, primary amides and secondary amides.
8. The method of 1, 2, 3, 4, 5, 6, 7 or 8, wherein the dialklyborane is selected from the group consisting of dicyclohexylborane, 9-borobicycloborane (9-BBN), disiamylborane, di(tert-butyl) borane, and diisopinocampheylborane.
9. The method of 1, 2, 3, 4, 5, 6, 7 or 8, wherein the functional group is reduced in less than about 5% of the product,
10. The method of 1, 2, 3, 4, 5, 6, 7 8 or 9, wherein the functional group is reduced in less than about 2% of the product.
11. The method of 1, 2, 3, 4, 5, 7, 8, 9 or 10, wherein the functional group is reduced in less than about 1% of the product,
12. The method of 1, 2, 3, 4 or 5 and 8, 9, 10 or 11, wherein the functional group is a carboxy ester group.
13. The method of 1, 2, 3, 4 or 5 and 8, 9, 10, 11 or 12, wherein the functional group is a methyl carboxy ester group.
14. The method of 1, 2, 3, 4 or 5 and 8, 9, 10 or 11, wherein the functional group is a ketone group.
15. The method of 1, 2, 6, 7 or 8, wherein the functional group is a hydroxyl group.
16. The method of 1, 2, 3, 4 or 5 and 8, 9, 10 or 11, wherein the functional group is a nitrile group.
17. The method of 1, 2, 6, 7 or 8, wherein the functional group is an amino group.
18. The method of 1, 2, 3, 4, 5, 6, 7, 8, 9, 10, 11, 12, 13, 14, 15, 16 or 17, wherein in step b) mixed substituted or unsubstituted trialkylborane or a (substituted or unsubstituted alkenyl) dialkylborane is contacted with a quinone in an ether solvent.

19. The method of 1, 2, 3, 4, 5, 6, 7, 8, 9, 10, 11, 12, 13, 14, 15, 16, 17 or 18, wherein the ether solvent is tetrahydrofuran.

20. The method of 1, 2, 3, 4, 5, 6, 7, 8, 9, 10, 11, 12, 13, 14, 15, 16, 17, 18 or 19, wherein steps a) and b) are carried out in an inert atmosphere.

21. The method of 1, 2, 3, 4, 5, 6, 7, 8, 9, 10, 11, 12, 13, 14, 15, 16, 17, 18, 19 or 20, wherein the inert atmosphere is nitrogen.

22. The method of 1, 2, 3, 5, 6, 7, 8, 9, 10, 11, 12, 13, 14, 15, 16, 17, 18, 19, 20 or 21, wherein the α,β-unsaturated carbonyl compound is p-benzoquinone.

23. The method of 1, 2, 3, 4, 5, 6, 7, 8, 9, 10, 11, 12, 13, 14, 15, 16, 17, 18, 19, 20, 21 or 22, wherein in step a) the reaction is carried out at a temperature from about 0 to about 30 degrees centigrade.

24. The method of 1, 2, 3, 4, 5, 6, 7, 8, 9, 10, 11, 12, 13, 14, 15, 16, 17, 18, 19, 20, 21, 22 or 23, wherein the temperature of the reaction in step a) is about 20 degrees centigrade.

25. The method of 1, 2, 3, 4, 5, 6, 7, 8, 9, 10, 11, 12, 13, 14, 15, 16, 17, 18, 19, 20, 21, 22, 23 or 24, wherein the temperature of the reaction in step b) the reaction is carried out at a temperature from about 0 to 30 degrees centigrade.

26. The method of 1, 2, 3, 4, 5, 6, 7, 8, 9, 10, 11, 12, 13, 14, 15, 16, 17, 18, 19, 20, 21, 22, 23, 24 or 25, wherein the temperature of the reaction in step b) is about 20 degrees centigrade.

27. The method of 1, 2, 3, 4, 5, 6, 7, 8, 9, 10, 11, 12, 13, 14, 15, 16, 17, 18, 19, 20, 21, 22, 23, 24, 25 or 26, wherein the regioselectivity is at least 95% in the product.

28. The method of 1, 2, 3, 4, 5, 6, 7, 8, 9, 10, 11, 12, 13, 14, 15, 16, 17, 18, 19, 20, 21, 22, 23, 24, 25, 26 or 27, wherein the regioselectivity is at least 99% in the product.

29. An substituted or unsubstituted alkyl or substituted or unsubstituted alkenyl boronic acid compound of the formula:

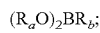

$(R_aO)_2BR_b$;

wherein $R_a$ is a hydrogen atom or an alkyl group, and $R_b$ is an alkyl or alkenyl group substituted with one or more aldehyde groups, further wherein when $R_b$ is an alkenyl group it is bound through one of the alkenyl carbons to the boron atom; and further wherein when $R_b$ is an alkyl group it is bonded by a unsubstituted methylene group to the boron atom; or a trifluoroborate salt thereof.

What is claimed is:

1. A method for synthesizing an substituted or unsubstituted alkylboronic acid or substituted or unsubstituted alkenyl boronic acid, comprising:
   a) contacting a dialkylborane with a compound comprising a compound selected from the group consisting of an substituted or unsubstituted terminal alkene, and substituted or unsubstituted alkyne to provide a mixed substituted or unsubstituted trialkylborane or an (substituted or unsubstituted alkenyl)dialkylborane;
   b) contacting the mixed substituted or unsubstituted trialkylborane or the (substituted or unsubstituted alk-enyl)dialkylborane of step a) with at least two equivalents of an α,β-unsaturated carbonyl compound to provide an substituted or unsubstituted alkyl boronate diester or an substituted or unsubstituted alkenyl boronate diester; and
   c) contacting either water or an alcohol with the boronate diester to quench the reaction and to yield a corresponding boronic acid compound product or a corresponding alkoxyboronate diester product.

2. A method of claim 1, wherein after step c) the boronic acid or boronate diester products is further reacted with potassium hydrogen difluoride to yield an substituted or unsubstituted alkyltrifluoroborate salt or an substituted or unsubstituted alkenyltrifluoroborate salt.

3. The method of claim 1, wherein the substituted or unsubstituted terminal alkene or the substituted or unsubstituted alkyne is substituted with a functional group containing one or more non-acidic proton substituents and the functional group is unprotected when it is contacted with the dialkylborane.

4. The method of claim 3, wherein the non-acidic proton substituents are selected from the group consisting of one or more aldehydes, ketones, carboxy esters, nitriles, lactams, lactones, and tertiary amides.

5. The method of claim 1, wherein the substituted or unsubstituted terminal alkene, or the substituted or unsubstituted alkyne, is substituted with a functional group containing one or more acidic protons and these one or more functional groups are also bonded to a protecting group such that the acidic proton on the functional group has been replaced by the protecting group.

6. The method of claim 1, wherein the dialklyborane is selected from the group consisting of dicyclohexlyborane, 9-borobicycloborane (9-BBN), disiamylborane, and diisopinocampheyborane.

7. The method of claim 3 or 5, wherein the functional group is reduced by less than about 5% in the product.

8. The method of claim 7, wherein the functional group is a carboxy ester group.

9. The method of claim 7, wherein the functional group is a ketone group.

10. The method of claim 7, wherein the functional group is a hydroxyl group.

11. The method of claim 7, wherein the functional group is a nitrile group.

12. The method of claim 7, wherein the functional group is an amino group.

13. The method of claim 1, wherein in step b) mixed substituted or unsubstituted trialkylborane or an (substituted or unsubstituted alkenyl) dialkylborane is contacted with the quinone in an ether solvent.

14. The method of claim 13, wherein the ether solvent is tetrahydrofuran.

15. The method of claim 1, 13, or 14, wherein the α, β-unsaturated carbonyl compound is p-benzoquinone.

16. The method of claim 1, 13, 14 or 15, wherein in step a) the reaction is carried out at a temperature from about 0 to about 30 degrees centigrade.

17. The method of claim 1, 13, 14, 15, or 16 wherein the temperature of the reaction in step b) the reaction is carried out at a temperature from about 0 to 30 degrees centigrade.

18. The method of claim 1, 13, 14, 15, 16, or 17, wherein the regioselectivity is at least 95% in the product.

* * * * *